United States Patent [19]
Winberry

[11] Patent Number: 5,989,564
[45] Date of Patent: Nov. 23, 1999

[54] PERTUSSIS TOXOID MADE BY REACTING PERTUSSIS TOXIN WITH THE NITRATING AGENT TNM

[75] Inventor: Larry K. Winberry, Brockton, Mass.

[73] Assignee: Massachusetts Health and Research Institute, Boston, Mass.

[21] Appl. No.: 07/759,822

[22] Filed: Sep. 12, 1991

Related U.S. Application Data

[63] Continuation of application No. 07/183,884, Apr. 20, 1988, abandoned.
[51] Int. Cl.$^6$ ............................ A61K 39/10; A61K 39/02
[52] U.S. Cl. ..................................... 424/254.1; 424/236.1; 424/240.1; 530/395; 530/405; 530/409
[58] Field of Search ........................... 424/92, 88, 254.1, 424/236.1, 240.1; 435/69.1, 822; 530/405, 413, 395, 409

[56] References Cited

U.S. PATENT DOCUMENTS

| 4,762,710 | 8/1988 | Sehura | 424/92 |
| 4,788,058 | 11/1988 | Parton et al. | 424/92 |

OTHER PUBLICATIONS

Everse et al, *Proc. Natl. Acad. Sci, USA,* vol. 74, pp. 472–476,1977.
Cuatrecasas et al, *J. Biological Chemistry,* vol. 243, pp. 4787–4798, 1968.
Riordan et al, *Methods in Enzymology,* vol. 25, pp. 515–521, 1972.
Das Gupta et al, *Proceedings from American Society for Microbiology,* pp. 33, 1986.
Beunier, (Arch, Int. Physical Biochem. vol. p.81, 1973.
Beugniier, Arch. Int. Physical. Biochem. vol. 80, pp. 389–390, 1972.
Everse et al, *Proc. Natl. Acad. Sci. U.S.A,* vol. 74, pp. 472–476, 1977.
Cuatrecasas et al, *J. Biological Chemistry,* vol. 243, pp. 4787–4798, 1968.
DasGupta and Woody, Proceedings from American Society for Microbiology p. 33, 1986.

Everse et al., Proc. Natl. Acad. Sci. USA 74:472–476, 1977.
Lauritzen et al., J. of Biological Chemistry 255:602–607, 1980.
Lane and Dekker, Biochemistry 11:3295–3303, 1972.
Cuatrecasas et al., J. Biological Chemistry 243:4787–4798, 1968.
Meyer et al., Biochemistry 18:3582–3587, 1979.
Riordan et al., Biochemistry 6:3609–3617, 1967.
Sokolovsky et al., Biochemistry 5:3582–3589, 1966.
Riordan and Vallee, Methods in Enzymology 25:515–521, 1972.
Riordan et al., J. American Chemical Society 88:4104–4105, 1966.
Fieser et al., Reagents for Organic Synthesis :1147–1148, 1969.
Woody and DasGupta, Molecular and Cellular Biochemistry 85:159–169, 1989.
Igarashi et al , "Chemical modification of staphylococcal enterotoxin B urth tetranitroructhane".
Proceedings of the 24th Syruposium on Toxins, Jap. J. Med. Sci., Biol. 31,21, 159–223, 1978.
Sato et al., "Bordetella pertussis Infection in Mice:," Infection and Immunity, 46:415–421 (1984).
Munoz et al., "Mouse–Protecting and Histamine–Sensitizing Activities of Pertussigen and Fimbrial Hemagglutinin from Bordetella pertussis," Infection and Immunity, 32:243–250 (1981).
Locht et al., "Pertussis Toxin Gene: Nucleotide Sequence and Genetic Organization," Science 232:1258–1264 (1986).
Armstrong et al., "Maintenance of Biological Activity of Pertussis Toxin Radioiodinated While Bound to Fetuin–Agarose," Infection and Immunity, 55:1294–1299 (1987).
Nicosia et al., "Cloning and sequencing of the pertussis toxin genes: Operon structure and gene duplication," Proc. Natl. Acad. Sci., 83: 4631–4635 (1986).

*Primary Examiner*—Cecilia J. Tsang
*Assistant Examiner*—Abdel A. Mohamed
*Attorney, Agent, or Firm*—Clark & Elbing, LLP

[57] ABSTRACT

A toxoid of pertussis toxin in which the pertussis toxin is modified essentially only at one or more tyrosine residues, as by the use of a nitrating agent such as tetranitromethane or by recombinant DNA techniques; a vaccine including the toxoid; and methods of preparing the toxoid and the vaccine.

8 Claims, 4 Drawing Sheets

```
EcoRI
GAATTCGTCGCCTCGCCCTGGTTCGCCGTCATGGCCCCCAAGGGAACCGACCCCAAGATA
                                  100
ATCGTCCTGCTCAACCGCCACATCAACGAGGCGCTGCAGTCCAAGGCGGTCGTCGAGGCC

TTTGCCGCCCAAGGCGCCACGCCGGTCATCGCCACGCCGGATCAGACCCGCGGCTTCATC
                200
GCAGACGAGATCCAGCGCTGGGCCGGCGTCGTGCGCGAAACCGGCGCCAAGCTGAAGTAG
                                                          300
CAGCGCAGCCCTCCAACGCGCCATCCCCGTCCGGCCGGCACCATCCCGCATACGTGTTGG

CAACCGCCAACGCGCATGCGTGCAGATTCGTCGTACAAAACCCTCGATTCTTCCGTACAT
                                  400
CCCGCTACTGCAATCCAACACGGCATGAACGCTCCTTCGGCGCAAAGTCGCGCGATGGTA
         ←
CCGGTCACCGTCCGGACCGTGCTGACCCCCCTGCCATGGTGTGATCCGTAAAATAGGCAC
         -35                                  -10
              500        S1
CATCAAAACGCAGAGGGGAAGACGGGATGCGTTGCACTCGGGCAATTCGCCAAACCGCAA
↑                         fM  R  C  T  R  A  I  R  Q  T  A
                                                           600
GAACAGGCTGGCTGACGTGGCTGGCGATTCTTGCCGTCACGGCGCCCGTGACTTCGCCGG
 R  T  G  W  L  T  W  L  A  I  L  A  V  T  A  P  V  T  S  P

CATGGGCCGACGATCCTCCCGCCACCGTATACCGCTATGACTCCCGCCCGCCGGAGGACG
 A  W  A  *D  D  P  P  A  T  V  Y  R  Y  D  S  R  P  P  E  D
                                       700
TTTTCCAGAACGGATTCACGGCGTGGGGAAACAACGACAATGTGCTCGACCATCTGACCG
 V  F  Q  N  G  F  T  A  W  G  N  N  D  N  V  L  D  H  L  T

GACGTTCCTGCCAGGTCGGCAGCAGCAACAGCGCTTTCGTCTCCACCAGCAGCAGCCGGC
 G  R  S  C  Q  V  G  S  S  N  S  A  F  V  S  T  S  S  S  R
               800
GCTATACCGAGGTCTATCTCGAACATCGCATGCAGGAAGCGGTCGAGGCCGAACGCGCCG
 R  Y  T  E  V  Y  L  E  H  R  M  Q  E  A  V  E  A  E  R  A
                                                          900
GCAGGGGCACCGGCCACTTCATCGGCTACATCTACGAAGTCCGCGCCGACAACAATTTCT
 G  R  G  T  G  H  F  I  G  Y  I  Y  E  V  R  A  D  N  N  F

ACGGCGCCGCCAGCTCGTACTTCGAATACGTCGACACTTATGGCGACAATGCCGGCCGTA
 Y  G  A  A  S  S  Y  F  E  Y  V  D  T  Y  G  D  N  A  G  R
                                     1000
TCCTCGCCGGCGCGCTGGCCACCTACCAGAGCGAATATCTGGCACACCGGCGCATTCCGC
 I  L  A  G  A  L  A  T  Y  Q  S  E  Y  L  A  H  R  R  I  P

CCGAAAACATCCGCAGGGTAACGCGGGTCTATCACAACGGCATCACCGGCGAGACCACGA
 P  E  N  I  R  R  V  T  R  V  Y  H  N  G  I  T  G  E  T  T
                    1100
CCACGGAGTATTCCAACGCTCGCTACGTCAGCCAGCAGACTCGCGCCAATCCCAACCCCT
 T  T  E  Y  S  N  A  R  Y  V  S  Q  Q  T  R  A  N  P  N  P
```

Fig. 1

```
                                                      .         .         1200
ACACATCGCGAAGGTCCGTAGCGTCGATCGTCGGCACATTGGTGCATGGCGCCGGTGATA
 Y  T  S  R  R  S  V  A  S  I  V  G  T  L  V  H  G  A  G  D

GCGCTTGCATGGCGCGGCAGGCCGAAAGCTCCGAGGCCATGGCAGCCTGGTCCGAACGCG
 S  A  C  M  A  R  Q  A  E  S  S  E  A  M  A  A  W  S  E  R
                         .         1300        .
CCGGCGAGGCGATGGTTCTCGTGTACTACGAAAGCATCGCGTATTCGTTCTAGACCTGGC
 A  G  E  A  M  V  L  V  Y  Y  E  S  I  A  Y  S  F  U
               .                   . [S2]→         .
CCAGCCCCGCCCAACTCCGGTAATTGAACAGCATGCCGATCGACCGCAAGACGCTCTGCC
                                 fM  P  I  D  R  K  T  L  C
               1400       .                  .
ATCTCCTGTCCGTTCTGCCGTTGGCCCTCCTCGGATCTCACGTGGCGCGGGCCTCCACGC
 H  L  L  S  V  L  P  L  A  L  L  G  S  H  V  A  R  A *S  T
                                                  .         1500
CAGGCATCGTCATTCCGCCGCAGGAACAGATTACCCAGCATGGCAGCCCCTATGGACGCT
 P  G  I  V  I  P  P  Q  E  Q  I  T  Q  H  G  S  P  Y  G  R

GCGCGAACAAGACCCGTGCCCTGACCGTGGCGGAATTGCGCGGCAGCGGCGATCTGCAGG
 C  A  N  K  T  R  A  L  T  V  A  E  L  R  G  S  G  D  L  Q
                              .         1600       .
AGTACCTGCGTCATGTGACGCGCGGCTGGTCAATATTTGCGCTCTACGATGGCACCTATC
 E  Y  L  R  H  V  T  R  G  W  S  I  F  A  L  Y  D  G  T  Y

TCGGCGGCGAATATGGCGGCGTGATCAAGGACGGAACACCCGGCGGCGCATTCGACCTGA
 L  G  G  E  Y  G  G  V  I  K  D  G  T  P  G  G  A  F  D  L
              1700        .                  .
AAACGACGTTCTGCATCATGACCACGCGCAATACGGGTCAACCCGCAACGGATCACTACT
 K  T  T  F  C  I  M  T  T  R  N  T  G  Q  P  A  T  D  H  Y
                                                  .         1800
ACAGCAACGTCACCGCCACTCGCCTGCTCTCCAGCACCAACAGCAGGCTATGCGCGGTCT
 Y  S  N  V  T  A  T  R  L  L  S  S  T  N  S  R  L  C  A  V

TCGTCAGAAGCGGGCAACCGGTCATTGGCGCCTGCACCAGCCCGTATGACGGCAAGTACT
 F  V  R  S  G  Q  P  V  I  G  A  C  T  S  P  Y  D  G  K  Y
                              .         1900       .
GGAGCATGTACAGCCGGCTGCGGAAAATGCTTTACCTGATCTACGTGGCCGGCATCTCCG
 W  S  M  Y  S  R  L  R  K  M  L  Y  L  I  Y  V  A  G  I  S

TACGCGTCCATGTCAGCAAGGAAGAACAGTATTACGACTATGAGGACGCAACGTTCGAGA
 V  R  V  H  V  S  K  E  E  Q  Y  Y  D  Y  E  D  A  T  F  E
                          .         2000       .
CTTACGCCCTTACCGGCATCTCCATCTGCAATCCTGGATCATCCTTATGCTGAGACGCTT
 T  Y  A  L  T  G  I  S  I  C  N  P  G  S  S  L  C  U
                                            [S4]→ 2100
CCCCACTCGAACCACCGCCCCGGGACAGGGCGGCGCCCGGCGGTCGCGCGTGCGCGCCCT
                                 fM  R  A  L
```

Fig. 2

```
GGCGTGGTTGCTGGCATCCGGCGCGATGACGCATCTTTCCCCCGCCCTGGCCGACGTTCC
  A  W  L  L  A  S  G  A  M  T  H  L  S  P  A  L  A  *D  V  P
                                    2200
TTATGTGCTGGTGAAGACCAATATGGTGGTCACCAGCGTAGCCATGAAGCCGTATGAAGT
  Y  V  L  V  K  T  N  M  V  V  T  S  V  A  M  K  P  Y  E  V
CACCCCGACGCGCATGCTGGTCTGCGGCATCGCCGCCAAACTGGGCGCCGCGGCCAGCAG
  T  P  T  R  M  L  V  C  G  I  A  A  K  L  G  A  A  A  S  S
             2300
CCCGGACGCGCACGTGCCGTTCTGCTTCGGCAAGGATCTCAAGCGTCCCGGCAGCAGTCC
  P  D  A  H  V  P  F  C  F  G  K  D  L  K  R  P  G  S  S  P
                                                          2400
CATGGAAGTCATGTTGCGCGCCGTCTTCATGCAACAACGGCCGCTGCGCATGTTTCTGGG
  M  E  V  M  L  R  A  V  F  M  Q  Q  R  P  L  R  M  F  L  G
TCCCAAGCAACTCACTTTCGAAGGCAAGCCCGCGCTCGAACTGATCCGGATGGTCGAATG
  P  K  Q  L  T  F  E  G  K  P  A  L  E  L  I  R  M  V  E  C
                                         S5→
CAGCGGCAAGCAGGATTGCCCCTGAAGGCGAACCCCATGCATACCATCGCATCCATCCTG
  S  G  K  Q  D  C  P  U            fM  H  T  I  A  S  I  L
TTGTCCGTGCTCGGCATATACAGCCCGGCTGACGTCGCCGGCTTGCCGACCCATCTGTAC
  L  S  V  L  G  I  Y  S  P  A  D  V  *A  G  L  P  T  H  L  Y
             2600
AAGAACTTCACTGTCCAGGAGCTGGCCTTGAAACTGAAGGGCAAGAATCAGGAGTTCTGC
  K  N  F  T  V  Q  E  L  A  L  K  L  K  G  K  N  Q  E  F  C
                                                          2700
CTGACCGCCTTCATGTCGGGCAGAAGCCTGGTCCGGGCGTGCCTGTCCGACGCGGGACAC
  L  T  A  F  M  S  G  R  S  L  V  R  A  C  L  S  D  A  G  H
GAGCACGACACGTGGTTCGACACCATGCTTGGCTTTGCCATATCCGCGTATGCGCTCAAG
  E  H  D  T  W  F  D  T  M  L  G  F  A  I  S  A  Y  A  L  K
                                    2800
AGCCGGATCGCGCTGACGGTGGAAGACTCGCCGTATCCGGGCACTCCCGGCGATCTGCTC
  S  R  I  A  L  T  V  E  D  S  P  Y  P  G  T  P  G  D  L  L
GAACTGCAGATCTGCCCGCTCAACGGATATTGCGAATGAACCCTTCCGGAGGTTTCGACG
  E  L  Q  I  C  P  L  N  G  Y  C  E  U
             2900
TTTCCGCGCAATCCGCTTGAGACGATCTTCCGCCCTGGTTCCATTCCGGGAACACCGCAA
                                                 S3→        3000
CATGCTGATCAACAACAAGAAGCTGCTTCATCACATTCTGCCCATCCTGGTGCTCGCCCT
 fM  L  I  N  N  K  K  L  L  H  H  I  L  P  I  L  V  L  A  L
GCTGGGCATGCGCACGGCCCAGGCCGTTGCGCCAGGCATCGTCATCCCGCCGAAGGCACT
  L  G  M  R  T  A  Q  A  *V  A  P  G  I  V  I  P  P  K  A  L
                                         3100
GTTCACCCAACAGGGCGGCGCCTATGGACGCTGCCCGAACGGAACCCGCGCCTTGACCGT
  F  T  Q  Q  G  G  A  Y  G  R  C  P  N  G  T  R  A  L  T  V
```

Fig. 3

```
GGCCGAACTGCGCGGCAACGCCGAATTGCAGACGTATTTGCGCCAGATAACGCCCGGCTG
  A   E   L   R   G   N   A   E   L   Q   T   Y   L   R   Q   I   T   P   G   W
                        3200          .           .           .           .           .
GTCCATATACGGTCTCTATGACGGTACGTACCTGGGCCAGGCGTACGGCGGCATCATCAA
  S   I   Y   G   L   Y   D   G   T   Y   L   G   Q   A   Y   G   G   I   I   K
                                                                    3300
GGACGCGCCGCCAGGCGCGGGGTTCATTTATCGCGAAACTTTCTGCATCACGACCATATA
  D   A   P   P   G   A   G   F   I   Y   R   E   T   F   C   I   T   T   I   Y
CAAGACCGGGCAACCGGCTGCGGATCACTACTACAGCAAGGTCACGGCCACGCGCCTGCT
  K   T   G   Q   P   A   A   D   H   Y   Y   S   K   V   T   A   T   R   L   L
                                  3400
CGCCAGCACCAACAGCAGGCTGTGCGCGGTATTCGTCAGGGACGGGCAATCGGTCATCGG
  A   S   T   N   S   R   L   C   A   V   F   V   R   D   G   Q   S   V   I   G
AGCCTGCGCCAGCCCGTATGAAGGCAGGTACAGAGACATGTACGACGCGCTGCGGCGCCT
  A   C   A   S   P   Y   E   G   R   Y   R   D   M   Y   D   A   L   R   R   L
              3500
GCTGTACATGATCTATATGTCCGGCCTTGCCGTACGCGTCCACGTCAGCAAGGAAGAGCA
  L   Y   M   I   Y   M   S   G   L   A   V   R   V   H   V   S   K   E   E   Q
                                                                    3600
GTATTACGACTACGAGGACGCCACATTCCAGACCTATGCCCTCACCGGCATTTCCCTCTG
  Y   Y   D   Y   E   D   A   T   F   Q   T   Y   A   L   T   G   I   S   L   C
CAACCCGGCAGCGTCGATATGCTGAGCCGCCGGCTCGGATCTGTTCGCCTGTCCATGTTT
  N   P   A   A   S   I   C   U
                                          3700
TTCCTTGACGGATACCGCGAATGAATCCCTTGAAAGACTTGAGAGCATCGCTACCGCGCC
TGGCCTTCATGGCAGCCTGCACCCTGTTGTCCGCCACGCTGCCCGACCTCGCCCAGGCCG
              3800
GCGGCGGGCTGCAGCGCTGTCAACCACTTCATGGCGAGCATCGTGGTCGTACTGCCGCGG
                                                          3900
CGGTCAGTGGCCACGGTGACCATCGCCATAATCTGGGCGGGCTACAAGCTGCTGTTCCGG
CACGCCGATGTGCTGGACGTGGTGCGTGTGGTGCTGGCGGGAGCTGCTGATCGGCGCATC
                                          4000
GGCCGAAATCGCTCGTTATCTGCTGACCTGAATCCTGGACGTATCGAACATGCGTGATCC
GCTTTTCAAGGGCTGCACCCGGCGCCGCGATGCTGATGGCGTACCCGCCACGGCAGGCCG
GCTTTTCAAGGGCTGCACCCGGCGCCGCGATGCTGATGGCGTACCCGCCACGGCAGGCCG
    ──────▶.         4100
TGTGCAGCCGGCACCATTCCCTGCTGGGCCATCTCGGTTCAGCATCCGCTTTCTGGCCTT
                                                                    4200
GTTTCCCGTGGCATTGCTGGCGATGCGGATCATGATCCGGCGCGATGACCAGCAGTTCCG
    Sau3A
CCT GATC
```

Fig. 4

PERTUSSIS TOXOID MADE BY REACTING PERTUSSIS TOXIN WITH THE NITRATING AGENT TNM

This is a continuation of application Ser. No. 07/183,884 filed on Apr. 20, 1988, now abandoned.

BACKGROUND OF THE INVENTION

This invention relates to the development of antigens suitable as vaccines for preventing whooping-cough.

Whooping-cough is a severe, highly contagious respiratory disease resulting from infection with the bacterium *Bordetella pertussis*. At the present time there is no fully effective treatment, the disease is associated with substantial morbidity and mortality, and is widespread throughout the world. Whooping-cough is particularly severe in infants.

Sato et al. 46 *Infect. & Immunity* 422, 1984 describe the use of whole-cell vaccines for controlling whooping cough, and their recent replacement by defined vaccines:

> Pertussis vaccine composed of killed cells has been playing a role in the reduction of whooping cough for more than 40 years throughout the world. At the same time, however, it is one of the most rejected of vaccines because of its adverse reactions. It is now time that the whole-cell vaccine be replaced by a more defined vaccine that is composed of specific components and is able to have its protective potency evaluated by means of purified reference protective antigens or antibodies. In Japan, a pertussis vaccine in use since 1981 has had some adverse effects reduced by removal of the endotoxin from a fraction of culture supernatant of *Bordetella pertussis* phase I cells and inactivation of some of the toxicity with Formalin. The main components of the vaccine are formalinized pertussis toxin (PT) and filamentous hemagglutinin (FHA). Now we understand that PT is the most potent antigen and FHA is a helpful protective antigen and that their antibodies play an important role in protecting mice from infection and disease caused by the pathogen.

To prepare such defined vaccines PT and FHA are purified by successive column chromatography procedures. Sato et al., Id. The PT and FHA is then treated with 0.2% formalin at 39° C., and with 0.1% formalin two more times every other day, prior to dialysis. Id. at 415.

An alternative procedure involves preparation of PT free of FHA, and subsequent treatment of PT with 0.05% glutaraldehyde to yield detoxified PT, which is effective in protecting mice from infection. Munoz et al. 32 *Infect & Immun.* 243, 1981.

The terminology used to define pertussis toxin is confused in the literature. PT is "also known as lymphocytosis-histamine-sensitizing factor, islet-activating protein, and pertussigen." Locht et al. 232 *Science*, 1258, 1986. Recently Armstrong et al. 55 *Infect & Immun.*, 1294, 1987 have described PT as follows:

> PT is a heterohexameric protein consisting of five subunits, designated $S_1$ to $S_5$ Based on their gene sequences, the molecular weights of the subunits are 26,024 for $S_1$, 21,925 for $S_2$, 21,873 for $S_3$, 12,058 for $S_4$, and 11,013 for $S_5$. The largest of the subunits, $S_1$, is responsible for ADP-ribosylating the α subunits of a family of homologous, guanine nucleotide-dependent regulatory complexes (designated G or N) in eucaryotic cells. The other four subunits are thought to form a pentameric base unit composed of two dimers ($S_2S_4$ [dimer 1] and $S_3S_4$ [dimer 2] which are connected to each other by the $S_5$ subunit. The function of the base structure is in binding to host cell receptors and providing a means for the $S_1$ subunit to penetrate the cytoplasmic membrane. [Citations omitted.]

Serine, threonine, and tyrosine residues are represented more frequently in PT than in average *E. coli* proteins. (Locht et al. Science 232: 1258, 1986.) It is thought that the hydroxyl groups of these residues may be involved in the quaternary structure of PT, through hydrogen bonding. Locht et al., Id. There are no lysine residues in the $S_1$ subunit of the PT gene which "may explain why lysine-specific chemical modification do not affect the hydroxyl and enzymatic activities of S1." Locht et al., Id.

Nicosia et al., 83 Proc. Nat. Acad. Sci. U.S.A. 4631, 1986, note that harsh conditions for inactivation of PT are required because of the shortage of lysine residues in subunit S1.

> The S1 subunit is one of the few proteins that does not contain lysine residues. This observation has important implications for the development of a new vaccine against pertussis, since normally for vaccine preparation, bacterial toxins are detoxified with chemicals that react mainly with lysine residues. Accordingly, we have observed that the detoxification of PT requires more severe conditions that those used for the other bacterial toxins and that following treatment with glutaraldehyde, S2, S3, S4 and S5 are crosslinked and form aggregates of high molecular weight, while S1 retains its original size.

PT is described as sensitive to iodination, but such sensitivity can be reduced by adsorption to fetuin-agarose. Armstrong et al. supra. One possible reason for this sensitivity is the large number of tyrosine residues in PT, some of which may be critical to its functions as a toxin. In conventional iodination research, the modification of such important tyrosines could be one explanation for loss of activity. Armstrong et al. Id.

Recently, the cloning of DNA encoding PT subunits has been described. Locht et al. supra; Nicosia et al., supra. Locht et al. note the use of such a gene for developing vaccines:

> The cloned and sequenced pertussis toxin gene will facilitate the development of an efficient and safer vaccine against whooping cough. By comparison to other toxin genes with similar biochemical functions, and by physical identification of the active sites either for the ADP-ribosylation in the S1 subunit or the target cell binding in subunits S2 through S4, it is now possible to modify those sites by site-directed mutagenesis of the *B. pertussis* genome. These modifications could abolish the pathobiological activities of pertussis toxin without hampering its immunogenicity and protectivity. Alternatively, by knowing the DNA sequence it will be possible to map protective epitopes. Synthetic oligopeptides that include those epitopes also will be useful in the development of a new generation of vaccines.

SUMMARY OF THE INVENTION

In a first aspect, the invention features a toxoid suitable as a vaccine for preventing whooping cough in a human, the toxoid including a polypeptide wherein the polypeptide retains sufficient antigenicity so as to be capable of competing for greater than 80% of the binding activity of polyclonal antitoxin antibody when tested at a concentration of 5 μg/ml in a standard competitive enzyme-linked immunosorbent assay (ELISA), and the toxoid shows no propensity for reversion to toxicity upon standing at 37° C. for a period of 8 weeks as assessed by the Chinese hamster ovary (CHO) cell assay.

In preferred embodiments, injection of 37.5 μg of the polypeptide into a 500 g guinea pig elicits production of neutralizing antibody equivalent to a titer of at least 1/200 when measured by the CHO cell neutralization assay, and the toxoid, when assayed for biological activity exhibits less than 0.0005% of the toxin activity of pertussis toxin as determined by the CHO-cell assay; the toxoid causes no deaths in the Histamine Sensitization Factor (HSF) activity assay when tested at IV doses of at least 30 μg/mouse; the toxoid has no more than 1% of the original hemagglutination activity as determined with goose red blood cells (RBCs); the toxoid has less than 5% of the original adenosine diphosphate (ADP)-ribosylase activity; the toxoid shows no propensity for reversion upon standing at 37° C. for a period of 8 weeks as assessed by the HSF or HA assays; the toxoid is prepared by reacting pertussis toxin with a nitrating agent, most preferably tetranitromethane (TNM).

In another related aspect, the invention features a toxoid suitable as a vaccine for preventing whooping cough in a human, the toxoid including pertussis toxin modified essentially only at tyrosine residues. Preferably, the pertussis toxin is modified by treatment with tetranitromethane. The invention also features a toxoid prepared by reacting purified pertussis toxin with TNM.

In another related aspect, the invention features a method for preparing pertussis toxoid, including reacting purified pertussis toxin with a nitrating agent, e.g., TNM.

In yet another aspect, the invention features a method for preventing whooping cough in a human including administering an immunizing amount of the toxoid to the human.

Other features and advantages of the invention will be apparent from the following description of the preferred embodiments thereof, and from the claims.

DESCRIPTION OF THE PREFERRED EMBODIMENTS

The drawing will first briefly be described.

DRAWING

The FIGURE is the DNA sequence, and corresponding amino acid sequence, of a gene encoding pertussis toxin.

PERTUSSIS TOXIN (PT)

PT can be prepared by any standard procedure, for example as described in the above cited articles by Armstrong et al., 1987, and Sato et al., 1984. The preferred method of its production is described in detail below.

Any B. pertussis strain can be used as a source of pertussis toxin for toxoid preparation. For example, PT is prepared from B. pertussis strains: CSK2, 18323CI or 18334K1. Strain CSK2 is a kanamycin resistant derivative of strain CS obtained from Dr. Ron Sekura, generated by transposon mutagenesis. Strain 18334K1 is a kanamycin resistant derivative of the 18334 strain originally isolated by the Michigan Department of Public Health. Any strain known to produce pertussis toxin at 0.5–1.0 mg/L is suitable. Such strains are readily available from the ATCC (e.g., strain 18323) or from the OoBRR (e.g., Strains Tohama I or 165).

Frozen seed-stock cultures are prepared by inoculation of 100 ml of cyclodextrin-enriched C.L. media (shown in Table 1) with the growth from several B.G. plates.

This culture is used to seed a spinner flask containing 1 liter of media. After 24 hr., sterile glycerol is added to 20% and the suspension aliquoted into 40 ml portions, which are subsequently frozen at −70° C.

To initiate a seed culture for a fermentor run, two tubes of frozen culture are rapidly thawed and used to inoculate 1 liter of media in a 6 liter spinner flask. The growth from this culture is used to seed a 14 liter New Brunswick Microferm containing 9 liters of C.L. media. Cyclodextrin increases toxin yield.

TABLE 1

| Cyclodextrin-enriched C-L Media | |
| --- | --- |
| Component (Heat Stable) | g/liter |
| Tris | 6.0 |
| Casamino Acids-Difco certified | 10.0 |
| Sodium glutamate | 10.7 |
| Sodium chloride | 2.5 |
| Potassium phosphate-monobasic | 0.5 |
| Potassium chloride | 0.2 |
| Magnesium chloride-hexahydrate | 0.1 |
| Calcium chloride-dihydrate | 0.02 |
| Proline | 0.24 |
| Hepatakis (2,6-O-dimethyl)B-cyclodextrin | 1.0 |
| Antifoam C | 0.45 ml/l |

The above components are dissolved, brought to pH 7.6 with 5N HCl, diluted to final volume and sterilized by autoclaving.

| Component (Heat Labile) | g/liter |
| --- | --- |
| Niacin | 0.004 |
| Ferrous sulfate-heptahydrate | 0.01 |
| Cysteine | 0.04 |
| Glutathione | 0.15 |
| Ascorbate | 0.4 |
| Kanamycin | 0.06 |

The above heat labile components are dissolved, brought to a final volume to yield a 100× concentrate and sterilized by filtration through a disposable 0.2 micron Nalgene filter unit. For fermentor media, the level of Ferrous sulfate is reduced 10 fold.

Following inoculation, the culture is maintained at 36–37° C. and is vigorously agitated using an impellor speed of 400–600 rpm. Aeration is accomplished by air inflow via a ring sparger at a rate of 0.2 to 2.0 liter/min. The dissolved oxygen preferably is maintained above 40% saturation. (With extremely heavy growth such oxygen levels are not always attainable.) Cultures are allowed to grow for approximately 24–36 hrs., after which time a sample is removed for Gram staining and plating onto BG plates for CFU (colony forming units) determinations. The colonies which form on BG plates are also screened for hemolysin production to verify maintenance of the virulence phase throughout the fermentation run.

The fermentation broth is transferred to an Amicon DC-10L hollow-fiber ultrafiltration unit equipped with a single H5 P01-43 filter cartridge ($10^6$ mwt cut-off) and the cells removed to leave a filtrate.

Purification of PT is carried out by a modification of the procedure described by Sekura et al., 23 *J. Biol. Chem.* 14647 (1983). Briefly, the pertussis toxin present in the Amicon filtrate is adsorbed and eluted from Affi-Gel Blue. Prior to its initial use, and following each purification run, the Affi-gel blue resin is washed sequentially with 5 bed volumes of: pyrogen-free water (PFW), PFW, 0.5M sodium carbonate, PFW, and 2M sodium chloride. Between uses, the resin is kept stored at 4° C. in the final 2M sodium chloride wash with 0.01% thimerosol added as preservative. Prior to use, the resin is freed of thimerosol and sodium chloride with a PFW wash.

The toxin-containing eluate from the Affi-Gel Blue column is diluted two-fold with PFW and allowed to adsorb batchwise to fetuin-Sepharose with gentle stirring in a spinner flask. Approximately 0.5 ml packed gel is used for each mg of toxin that is estimated to be in the eluate. Prior to use, the resin is extensively washed with alternating cycles of 0.1M NaHCO$_3$, 0.5M NaCl pH 8.3 and 0.1M NaOAc, 0.5M Nacl pH 4.0 followed by PFW to eliminate the NaCl. After binding the toxin, the resin is poured into a column and washed with 10 bed volumes of 0.1M NaOAc, 0.5M NaCl pH 7.0. Toxin is eluted with the same buffer containing 4M MgCl$_2$.

The fetuin-eluate is freed of MgCl$_2$ by extensive dialysis against 0.025 M NaPO$_4$, 0.5 M NaCl, 4% glycerol. The pH of the dialysis buffer is adjusted to 8.7–8.9. No loss of biological activity was observed upon storage of toxin at this pH for several months.

Purity and toxicity of the prepared PT is tested as follows.

a. The ability of pertussis toxin to agglutinate goose red blood cells (RBCs) is determined by serially diluting the toxin with phosphate buffered saline (PBS) and then incubating each dilution with an equal volume of 0.5% goose RBCs. The endpoint is defined as the lowest toxin concentration giving complete agglutination. Endpoints of 100–200 ng/ml are typically observed.

b. Purified pertussis toxin is analyzed for purity by electrophoresis in the presence of SDS using the Laemmli buffer system. Preparations are considered homogeneous if they consist of subunits corresponding to S1 through S4/S5 and show no staining of protein bands indicative of extraneous protein contamination.

c. The level of contaminating endotoxin is determined by the LAL assay (see below). Preparations to be used for toxoid preparation contain less that 50 EU/mg of toxin.

PERTUSSIS TOXOID

Pertussis toxoid of the invention is similar enough to pertussis toxin so that it elicits an immunogenic response in a mammal, but dissimilar enough so that it does not exhibit PT's toxic effects. Generally, modifications for toxicity reduction must occur within the toxin S$_1$ subunit, and the B oligomer, as both enzymatic and binding function impart biological activity to the molecule.

The toxoid of the invention is prepared from PT by chemical modification to irreversibly convert PT to a stable, immunogenic toxoid. Most preferably, this modification is performed by treatment of PT with a nitrating agent such as TNM. This process is optimally performed in the presence of a detergent to maximize yields. For vaccine preparation, the detergent of choice is cholic acid (a naturally occuring serum constituent) at 1% concentration in a buffer having a pH above 7.0, most preferably at about pH 8.5. Other non-cytotoxic detergents are also suitable. Without being bound to any particular theory, applicants propose that these detergents act on PT to expose tyrosine residues for reaction with nitrating agents, such as TNM.

Alternatively, modified PT can be produced by genetic means, involving modifications of the nucleic acid encoding natural PT. Modification of the nucleic acid to convert one or more tyrosine codons, particularly in the DNA encoding S$_1$, to other codons, or by deleting these residues completely, may yield stable, non-toxic pertussis toxoid.

EXAMPLE 1

Chemical Modification of PT with TNM

A sub-lot of PT was thawed and aggregated PT removed by filtration through a 0.2 $\mu$M Gelman acrodisc. Protein concentration was adjusted to 220–240 $\mu$g/ml with dialysis buffer. Once the protein concentration was adjusted, 1/10th volume of 10% cholic acid was added to a toxin aliquot, so that the final concentration of cholate in the aliquot was 1%. With continuous mixing, 6% TNM in ethanol was added dropwise to the reaction until the final concentration of TNM was 0.12%. This mixture was then allowed to stand for 2 hours at room temperature (20–22° C.). The reaction was quenched by adding 1/100th volume of 1M DDT. The reaction mixture was subsequently dialyzed against 3×100 volume changes of dialysis buffet (0.5M NaCl, 4% glycerol, 0.025M NaPO$_4$, pH8.5); each change stands at least 24 hours at 4° C. In order to ensure acceptable toxoid recovery it is preferred that dialysis be performed at or above pH7.0, most preferably above pH8.5.

The toxoid solution was filtered through 0.2 micron Gelman polysulfone acodiscs. It was then stored at 4° C. and tested for sterility, residual activity, protein content and reversion, as discussed below.

To prepare the toxoid for vaccination it was adsorbed onto aluminium phosphate. When formulated as a final product, the preparation contains 0.90±05 mg/ml Al.

Briefly, adsorption was as follows: to a sterile spinner flask, final components were added in the following order: 1) 2× AlPO$_4$ gel containing 0.02% merthiolate, 2) fluid pertussis toxoid, and 3) 25 mM NaH$_2$PO$_4$ pH 5.–6.0 in appropriate volumes to yield a 1× AlPO$_4$ preparation containing 50 ug/ml toxoid and 0.01% merthiolate. The preparation was allowed to stir 1 hour at room temperature and overnight at 4° C. Samples were removed for sterility, reversion analysis, potency, and thimerosol determinations by standard procedures, as described below.

EXAMPLE 2

Mutation of PT Gene to Encode a Toxoid

Referring to the FIGURE, S$_1$ is encoded by DNA starting at the ATG codon (with S1 written above it) and extending to the TAG codon at base number 1313. Tyrosine codons are labelled Y. Proof that tyrosine residues are involved in the toxicity of S$_1$ is the above-demonstrated effectiveness of TNM in eliminating toxicity, i.e., converting the toxin into a toxoid. The same result can be attained by deleting one or more tyrosine codons, or by replacing one or more tyrosine codons with a non-aromatic amino acid codon.

Following are two examples of oligonucleotides suitable for modifying a region of S$_1$ to produce a toxoid. One skilled in the art will recognize that modification of S$_1$ is readily performed using these oligonucleotides, or other such oligonucleotides, and standard in vitro mutagenesis procedures, such as those described by Gait, Oligonucleotide Synthesis, A Practical Approach (ed. Gait) IRL Press Ltd., Oxford, UK, 1984, pp. 6–7), and references cited therein.

An oligonucleotide suitable for replacing the tyrosine residue at base position 796–799 (FIG. 1) is:

(base)  5' G A G G T C A A T C T C G A A C A T 3'  (base)
(789)          E   V   N   L   E   H              (808)

The letters below the oligonucleotide represent amino acids (using the standard one-letter code). In this oligonucleotide, the tyrosine at position 796–799 is replaced with asparagine (N). The underlined base represents the single base pair mutation which this oligonucleotode introduces.

An oligonucleotide suitable for deleting the tyrosine residue of base position 999–1001 (FIG. 1) is:

(base)  5' A G G G A A ___ C T G G C A C A C C G G 3'  (base)
(993)       S   E           L   A   H   R             (1013)

The line in the middle of this oligonucleotide represents a deleted region of three bases at 999–1001, and is not present in the oligonucleotide itself.

Briefly, to use these oligonucleotides to mutate the $S_1$ gene, the oligonucleotide is annealed to a template of circular M13 single stranded DNA encoding the natural pertussis toxin $S_1$ unit, extended using Klenow DNA polymerase and then ligated using T4-ligase. The double stranded molecule so formed is then used to transform an *E. coli* cell, and the resulting plaques isolated. DNA from these plaques encodes the desired mutant toxin.

Similar modifications of the other S-subunits can also provide useful toxoids.

The modified toxin gene is transformed into appropriate cells, and the toxoid expressed in these cells and then isolated by standard procedure. This toxoid is prepared for vaccination as described above for TNM-treated toxin.

Toxicity and Immunogenicity of TNM Toxoid

To assess toxin inactivation, we have assayed toxoids of the invention for residual hemagglutination activity, ribosylase activity, CHO-cell clustering and HSF activities.

a. Residual Hemagglutination (HA) Activity:

The ability of toxin to hemagglutinate goose red blood cells is thought to reflect the cell binding/attachment activity of the protein. This binding process has recently been shown to be sufficient to induce a mitogenic response in cultured human T-lymphoma cells. Consequently, it is preferable that any prospective toxoid be totally lacking in residual HA activity. Therefore prior to adsorption, all pertussis toxoids are tested for HA and should demonstrate no detectable activity in order to be considered adequately detoxified.

b. Residual Histamine Sensitization Factor (HSF) Activity:

The ability of pertussis toxin to sensitize mice to sublethal doses of histamine is an extremly sensitive bioassay. With a sensitivity of 1–2 ng/mouse, the HSF assay provides an in vivo system capable of detecting minute amounts of residual toxin activity. To be considered safe for human use, all pertussis toxoid vaccines, prior to adsorption, must be free of HSF activity when injected intraveneously (IV) into test mice at a dose of at least 30 ug/mouse. The standard protocol for this assay is given in Appendix 4.

c. Residual Chinese Hamster Ovary (CHO) Cell Clustering Activity:

Exposure of CHO cells to pg/ml concentrations of pertussis toxin elicits a morphological change that is reproducible and quantitatable. This change has been described as a clustering effect in which the cells lose their typical fibroblast shape and round up and form clumps. Because of the assay's sensitivity we have chosen to use it to screen toxoid preparations. As with the HA and HSF tests, to be acceptable as a toxoid the preparation preferably lacks CHO cell clustering activity when tested at concentrations of at least 10 ug/ml. The standard protocol and in process form for this assay is given in Appendix 5.

The results of this analysis for a clinical lot of pertussis toxoid of the invention (TNM-treated) are shown in Table 2. No binding activity was demonstrable as assessed by hemagglutination. The assay of A-protomer function (i.e., ribosylase activity) revealed a small (3.4%) residual activity. This activity alone appears not to confer any holotoxin toxin activity to the preparation as shown by the CHO cell and HSF results.

TABLE 2

Specific Biologic Activities of Pertussis Toxin and Its TNM-inactivated Product Pertussis Toxoid (Lot MAPT-1)

| Activity | Native Toxin | MAPT-1 Toxoid | % Residual Activity |
|---|---|---|---|
| Ribosylase (u/mg protein) | 1000 | 34.0 | 3.4 |
| HA activity (ng/ml) | 100 | >4.7 × $10^4$ | <0.5 |
| HSF activity | 2.2 | >3.76 × $10^4$ | <5.3 × $10^{-5}$ |
| CHO-cell clustering activity (pg/ml) | 2.2 | >1.88 × $10^7$ | <1.2 × $10^{-5}$ |

In order to establish the stability of the pertussis toxoid we have conducted an extensive reversion analysis of preparations, both as a fluid toxoid and also after adsorption to an aluminum phosphate adjuvant. The two preparations, fluid and adsorbed, are stress tested by incubation at 25° C. and 37° C. At 4 and 8 weeks each preparation is tested for HSF activity. In the case of the fluid toxoid, the equivalent of approximately 2 single human doses (38 μg) are injected IV into each of 20 mice. For adsorbed toxoid the mice are injected intraperitoneally (IP) with one single human dose (25 μg). The results of such tests are presented in Table 3. No indication of reversion was observed for either preparation.

TABLE 3

HSF Reversion Analysis of Fluid and Adsorbed Pertussis Toxoid

| Preparation | Dose/mouse | Survival of Histamine Challenge |
|---|---|---|
| Fluid MAPT-1 (IV) | | |
| 4 wks at 25° C. | 38 μg | 20/20 |
| at 37° C. | 38 μg | 20/20 |
| 8 wks at 25° C | 38 μg | 19/19 |
| at 37° C. | 38 μg | 19/19 |

TABLE 3-continued

HSF Reversion Analysis of Fluid
and Adsorbed Pertussis Toxoid

| Preparation | Dose/mouse | Survival of Histamine Challenge |
|---|---|---|
| Reference Toxin (IV) | | |
| | 8 ng | 0/7 |
| | 2 ng | 3/8 |
| | 0.5 ng | 7/7 |
| Adsorbed MAPT-1 (IP) | | |
| 4 wks at 25° C. | 25 μg | 21/21 |
| at 37° C. | 25 μg | 21/21 |
| 8 wks at 25° C. | 25 μg | 18/18 |
| at 37° C. | 27 μg | 18/18 |
| Reference Toxin (IP) | | |
| | 80 ng | 4/10 |
| | 20 ng | 3/11 |
| | 5 ng | 9/11 |

The fluid toxoid samples were also subjected to reversion testing using the CHO cell clustering assay. These results are presented in Table 4. As with the HSF results, no detectable instability is detected in the pertussis toxoid preparation.

TABLE 4

| MAPT-1 Preparation | CHO Toxicity[a] (μg/ml) | % Residual Activity |
|---|---|---|
| 4 wks at 4° C. | ≧18.8 (ND) | ≦2.4 × 10$^{-5}$ |
| at 25° C. | ≧18.8 (ND) | ≦2.4 × 10$^{-5}$ |
| at 37° C. | ≧18.8 (ND) | ≦2.4 × 10$^{-5}$ |
| 8 wks at 4° C. | ≧18.8 (ND) | ≦2.4 × 10$^{-5}$ |
| at 25° C. | ≧18.8 (ND) | ≦2.4 × 10$^{-5}$ |
| at 37° C. | ≧18.8 (ND) | ≦2.4 × 10$^{-5}$ |
| Toxin (pre-toxoid MAPT-1) | 4.5 × 10$^{-6}$ | 100 |

[a]Toxicity is reported as minimum protein concentration at which toxicity was observed.
ND = None detected at maximum concentration tested.

To determine the ability of the adsorbed pertussis toxoid to provoke an immune response 1.5 single human doses (37.5 μg) of the toxoid were injected into eight 500 g guinea pigs. At 4 and 6 weeks post-immunization the animals were bled and their anti-pertussis toxin titers determined by both an IgG-specific ELISA (see Appendix 3) and a CHO cell neutralization assay (see Appendix 11). Results, some of which are shown in Table 5, clearly demonstrate the immunogenic potential of the MAPT-1 preparation, which has a titer of over 1/400, after 6 weeks, in the CHO cell neutralization assay. For comparison the results obtained with a licensed DTP vaccine (lot 260) produced by the Biologics Laboratory, and an experimental vaccine produced by the Japanese National Institutes of Health (JNIH6), have also been included. JNIH6 is currently under clinical investigation in Sweden and appears to be efficacious. Thus, based on serologic response, the adsorbed pertussis toxoid vaccine of this invention appears to be a promising alternative to the current whole cell vaccine.

TABLE 5

| Results of Immunogenicity Testing of Pertussis Toxoid (MAPT-1) in Guinea Pigs | | | | |
|---|---|---|---|---|
| Vaccine | IgG ELISA* (μg/ml) | | CHO Cell Neut.* (l/dilution) | |
| (dose/G.P.) | 4 wks | 6 wks | 4 wks | 6 wks |
| MAPT-1 | 12.9 | 32.0 | 126 | 403 |
| DTP-260 (1.5 SHD) | 1.4 | 4.8 | 4 | 11 |
| JN1M6 (37.5 μg PT + 37.5 μg FHA) | 15.9 | 24.9 | 220 | 424 |

*Geometric mean antibody concentrations

Antigenicity of the TNM-toxoid was also determined by competitive ELISA using rabbit polyclonal anti-toxin sera. The standard operating procedure for this assay is presented in Appendix 1. (Another suitable procedure is described in Appendix 2, using Fetuin to bind residual toxin molecules.) This assay compares the ability of toxoid to compete for antibody binding with toxin that has been coated onto ELISA plates. Toxoid prepared with TNM retains most, if not all, antigenic determinants recognized by the rabbit antiserum. At a 5 μg/ml concentration, the toxoid is capable of competing for greater than 80% of the antibody binding capacity.

Other tests, suitable for determining the usefulness of a toxoid preparation, include testing for pyrogenicity, for residual TNM, for thimerosal, for residual lipopolysaccaride (LPS), for cholic acid, and for sterility. These were performed as follows:

a. Pyrogenicity Testing:

Using a dose of 5 ug/Kg, all fluid toxoid lots must preferably pass a standard rabbit pyrogen test. This dose approximates the predicted toxoid/infant weight ratio for a two-month old infant (5 Kg) and a toxoid formulation of 25 ug/SHD. The standard operating procedure for this test is given in Appendix 6.

b. Residual Tetranitromethane (TNM):

Prior to testing, the toxoided material is passed through an Amicon miniconcentrator and a TNM assay is performed on the filtrate. Tetranitromethane and its by-products are detected with the use of a colorimetric assay. Briefly, a 10% potassium iodide solution is reacted with an aliquot of the toxoid filtrate. In the presence of nitro groups the iodide develops a yellow color, due to iodine formation, which can be monitored at 410 nm. The sensitivity of this assay is 0.0006%. For acceptance, all toxoids preferably show no detectable TNM.

c. Thimerosal Determination:

Bulk toxoid is analyzed for thimerosal by the assays described in Appendix 9.

d. Residual Lipopolysaccharide (LPS) as Determined by the LAL Assay:

Fluid toxoids at a concentration of 50 ug/ml must contain less than about 2 *E. coli* endotoxin units/ml when tested in a standard LAL assay. This allows, at the upper limit, approximately 0.01 ng/ml *Bordetella pertussis* LPS contamination. On a LPS wt/protein basis this would be equivalent to a maximum contamination of about $2\times10^{-5}$%. (in the LAL assay, 1 ng *Bordetella pertussis* LPS=160 *E. coli* endotoxin units). The LAL assay is described in Appendix 8.

e. Residual Cholic Acid:

The standard assay is given in Appendix 10.

f. Bulk Sterility:

The standard protocol for sterility testing (steritest) of bulk adsorbed Pertussis Toxoid is by use of membrane filtration, described in Appendix 7.

Use

Once constructed, a toxoid of the invention is manufactured into a vaccine by standard procedures and administered orally or parenterally in a dose that is large enough to induce an immune response in the host. For example, 10–50 μg of toxoid is administered, by IP injection, three times to children of 3–24 months, with a booster after 3 years.

Other embodiments are within the following claims.

I claim:

1. A toxoid comprising pertussis toxin modified essentially only at one or more tyrosine residues such that said toxoid is immunogenic and not toxic.

2. The toxoid of claim 1, wherein said toxoid is prepared by reacting pertussis toxin with TNM so that one or more tyrosine residues of said pertussis toxin are nitrated.

3. A vaccine for preventing whooping cough in a human, said vaccine comprising the toxoid of claim 1.

4. The vaccine of claim 3, wherein said pertussis toxin is modified by treatment with TNM so that one or more tyrosine residues of said pertussis toxin are nitrated.

5. A toxoid prepared by reacting pertussis toxin with TNM so that one or more tyrosine residues of said pertussis toxin are nitrated to yield said toxoid that is immunogenic and not toxic.

6. A method for preventing whooping cough in a human, said method comprising administering an immunizing amount of the toxoid of claim 1, claim 2, or claim 5, to said human.

7. A method for preparing pertussis toxoid, said method comprising reacting pertussis toxin with TNM so that one or more tyrosine residues of said pertussis toxin are nitrated to yield said toxoid that is immunogenic and not toxic.

8. A method for preparing a vaccine for preventing whooping cough in a human, said method comprising modifying pertussis toxin essentially only at one or more tyrosine residues by reacting said toxin with TNM.

\* \* \* \* \*